United States Patent
Barden et al.

(10) Patent No.: US 9,623,886 B2
(45) Date of Patent: Apr. 18, 2017

(54) STEERING ASSIST SYSTEM FOR A PUSH CART

(71) Applicant: Howard Industries, Ellisville, MS (US)

(72) Inventors: Tim Barden, Stringer, MS (US); Jared Huguet, Petal, MS (US); Jason Neal, Laurel, MS (US); Tony Thornton, Hattiesburg, MS (US)

(73) Assignee: HOWARD INDUSTRIES, Ellisville, MS (US)

( * ) Notice: Subject to any disclaimer, the term of this patent is extended or adjusted under 35 U.S.C. 154(b) by 0 days.

(21) Appl. No.: 15/048,425

(22) Filed: Feb. 19, 2016

(65) Prior Publication Data

US 2016/0244080 A1    Aug. 25, 2016

Related U.S. Application Data

(60) Provisional application No. 62/119,252, filed on Feb. 22, 2015.

(51) Int. Cl.
*B62B 5/04* (2006.01)
*B62B 3/00* (2006.01)
(Continued)

(52) U.S. Cl.
CPC .............. *B62B 3/001* (2013.01); *A61B 50/13* (2016.02); *A61B 50/15* (2016.02); *B62B 3/10* (2013.01);
(Continued)

(58) Field of Classification Search
CPC .... B62B 5/0404; B62B 5/0423; B62B 5/0438
See application file for complete search history.

(56) References Cited

U.S. PATENT DOCUMENTS

| 4,084,663 A | * | 4/1978 | Haley | ....................... B62B 5/04 188/19 |
| 4,976,447 A | * | 12/1990 | Batson | ....................... B62B 5/04 188/19 |

(Continued)

OTHER PUBLICATIONS

Jared Huguet et al., "Adjustable Handle System for a Push Cart," U.S. Appl. No. 62/119,258, filed Feb. 22, 2015.

*Primary Examiner* — Erez Gurari
(74) *Attorney, Agent, or Firm* — Finnegan, Henderson, Farabow, Garrett & Dunner, LLP

(57) ABSTRACT

A steering assist system (SAS) for a cart is provided. The SAS may include an activation mechanism, a first actuation mechanism, a first support mechanism, a first linkage mechanism, a first stopping mechanism, and a first engagement mechanism. The first stopping mechanism may be configured to abut the first engagement mechanism to impede or prevent rotational movement of at least one wheel of the cart. The first actuation mechanism may be connected to the first linkage mechanism and the first linkage mechanism may be connected to the first stopping mechanism. The activation mechanism may be configured to activate the first actuation mechanism, causing the first linkage mechanism and the first stopping mechanism to move. The first stopping mechanism may be configured to move between a fully activated position and a fully deactivated position.

17 Claims, 13 Drawing Sheets

(51) Int. Cl.
*B62B 3/10* (2006.01)
*A61B 50/13* (2016.01)
*A61B 50/15* (2016.01)

(52) U.S. Cl.
CPC .......... *B62B 5/0404* (2013.01); *B62B 5/0423* (2013.01); *B62B 5/0438* (2013.01); *B62B 2202/56* (2013.01); *B62B 2301/046* (2013.01)

(56) References Cited

U.S. PATENT DOCUMENTS

| | | | | |
|---|---|---|---|---|
| 5,288,089 A * | 2/1994 | Bowers | ................ | B62B 3/1492 188/19 |
| D362,529 S * | 9/1995 | Hilaire, Jr. | ................ | 280/33.994 |
| 5,576,691 A * | 11/1996 | Coakley | ................ | B60B 33/021 188/111 |
| 5,806,862 A * | 9/1998 | Merryman | ............ | B62B 5/0423 188/111 |
| 5,979,917 A * | 11/1999 | Thogersen | .......... | B60B 33/0018 188/19 |
| 6,419,053 B1 * | 7/2002 | Martin-Vegue | ........... | B62B 5/04 188/19 |
| 7,255,206 B1 * | 8/2007 | Hackbarth | ................ | B62B 5/04 188/19 |
| 7,267,349 B2 * | 9/2007 | Sica | ....................... | B60G 3/185 187/222 |
| 7,396,026 B1 * | 7/2008 | Munson | .................... | B62B 5/04 188/2 D |
| 7,401,796 B1 * | 7/2008 | Greco | .................... | A47B 21/00 280/47.34 |
| 7,448,476 B2 * | 11/2008 | Otterson | ................... | B62B 5/04 188/19 |
| 7,562,729 B2 * | 7/2009 | Hammerle | .............. | B60R 25/00 180/65.1 |
| 8,562,003 B2 * | 10/2013 | Reep | ..................... | B62B 5/0438 188/19 |
| 8,764,032 B1 * | 7/2014 | Dantice | ................. | B62B 5/0404 280/47.35 |
| 2011/0202367 A1 * | 8/2011 | Frangioni | .............. | G06Q 50/24 705/3 |
| 2012/0126503 A1 * | 5/2012 | Butler | ................. | A61G 12/001 280/47.35 |
| 2014/0184038 A1 * | 7/2014 | Shoenfeld | ........... | G07C 9/00111 312/209 |

* cited by examiner

STEERING ASSIST SYSTEM FOR A PUSH CART

CROSS-REFERENCE TO RELATED APPLICATION

This application claims the benefit of and incorporates by reference, in its entirety, the contents of U.S. Provisional Application No. 62/119,252, filed Feb 22, 2015, and entitled "STEERING ASSIST SYSTEM FOR A PUSH CART." This application further incorporates by reference, in its entirety, the contents of U.S. Provisional Application No. 62/119,258, filed Feb 22, 2015 (now U.S. application Ser. No. 15/048,436, filed Feb. 19, 2016), and entitled "ADJUSTABLE HANDLE SYSTEM FOR A PUSH CART."

FIELD OF THE DISCLOSURE

Embodiments of the present disclosure include a mobile machine, such as, for example, a push cart. The push cart may be used, for example, in the health-care industry. More particularly, the present disclosure relates to a point-of-care medical cart having a steering assist system (SAS) for improved control over the cart while the cart is being moved. Though the disclosure will primarily refer to the SAS in conjunction with a medical cart in a health-care environment, it should be appreciated that the SAS may be incorporated into other mobile machines and that the SAS and/or push cart may be used in other non-health care environments.

BACKGROUND OF THE DISCLOSURE

Medical carts are among the most widespread tools used in the health care industry, and similar push carts are increasingly being used in other environments, such as factories, garages, workshops, and offices. Medical carts are designed for a variety of uses and environments, but some function, e.g., as mobile computing workstations that allow health-care professionals to access, input, and distribute patients' medical information and/or medical treatment. For example, a nurse or other medical practitioner may use a medical cart equipped with a computer and/or diagnostic equipment while making rounds between patients in a hospital or other care facility. The practitioner may use the computer, e.g., to review a patient's medication information, record vital signs and other notes, and order treatment. Medical carts may be equipped with tools for diagnosis and treatment, and/or store and dispense medication. Regardless of the carts specific purpose, however, the cart must be configured to move quickly but safely through a health-care environment.

Providing a medical cart that can easily move through such a health-care environment presents several challenges. For example, modern medical carts often include a computer, display screens, an adjustable keyboard, an independent power system, extra-capacity batteries, large height-adjustable work-surfaces, and storage for medication or equipment—weighing tens to hundreds of pounds. The mass of the cart may make it difficult to control in tight areas, such as hospital rooms. Injuries are more likely to occur if the cart is not ergonomically designed. Although various "battery-assisted" solutions for improving control and maneuverability exist, they do not fully address the problem.

In order to provide mobility in tight spaces, such carts may include, for example, four caster wheels (two in the front and two in the rear), each of which may freely swivel 360° to allow for greater mobility. While the use of caster wheels may make it easier to move a cart sideways or in a tight area, caster wheels led to other drawbacks. For example, the cart's heavy weight and the caster wheels' freedom of rotation combine to make it difficult to change the direction of the mass of the cart in motion, e.g., when turning corners and to follow a straight path or move from one side to the other while traveling down a hallway (particularly a hallway with uneven floors). Therefore, there exists a need for designs that improve control, safety, and ergonomic comfort during movement of the cart.

SUMMARY OF THE DISCLOSURE

In the following description, certain aspects and embodiments of the present disclosure will become evident. It should be understood that the disclosure, in its broadest sense, could be practiced without having one or more features of these aspects and embodiments. It should also be understood that these aspects and embodiments are merely exemplary.

In accordance with an embodiment, a SAS for a cart may include an activation mechanism, a first actuation mechanism, a first support mechanism, a first linkage mechanism, a first stopping mechanism, and a first engagement mechanism. The first stopping mechanism may be configured to abut the first engagement mechanism to impede or prevent rotational movement of at least one wheel of the cart. The first actuation mechanism may be connected to the first linkage mechanism and the first linkage mechanism may be connected to the first stopping mechanism. The activation mechanism may be configured to activate the first actuation mechanism, causing the first linkage mechanism and the first stopping mechanism to move. The first stopping mechanism may be configured to move between a fully activated position and a fully deactivated position.

In accordance with another embodiment, a SAS for a cart may include a first and/or a second activation mechanism, a first and a second actuation mechanism, a first and a second support mechanism, a first and a second linkage mechanism, a first and a second stopping mechanism, and a first and a second engagement mechanism. The first and second stopping mechanisms may be configured to abut the first and second engagement mechanisms to impede or prevent rotational movement of a plurality of wheels of the cart.

In accordance with another embodiment, a SAS for a cart may include an activation mechanism, wherein the activation mechanism may include a data measuring device, a real-time location system, a voice-activation system, and/or a push button. The SAS may also include an actuation mechanism that includes an electric motor and a lever arm. The SAS may also include a linkage mechanism that includes a rod, at least one resistive element, a driving element, and at least one retaining element. The SAS may also include a stopping mechanism that includes a latch, which may be rotatably attached to a frame element having a frame cover. The SAS may also include an engagement mechanism that includes a caster cap, and the caster cap may include a ramp and an engagement portion configured to contact the stopping mechanism.

In accordance with another embodiment, a SAS for a cart may include an activation mechanism, an actuation mechanism, and a stopping mechanism. The activation mechanism may be configured to automatically activate the actuation mechanism to move the stopping mechanism from a first position to a second position, thereby preventing or impeding rotation of at least one wheel of the cart. The SAS may also include a linkage mechanism that includes a rod, a drive pin, a first retaining washing and a second retaining washer, and a first spring and a second spring. The first retaining washer may be configured to hold the first spring captive on a first side of the drive pin, and the second retaining washer may be configured to hold the second spring captive on a second side of the drive pin. The SAS may also include an engagement mechanism having a cross section shaped like a nautilus shell, and the engagement mechanism may be configured to contact the stopping mechanism to prevent or impede rotation of at least one wheel of the cart.

In accordance with yet another embodiment, a cart may include a computer mounted below a horizontal work surface, a display screen mounted above the horizontal work surface, a control panel coupled to the horizontal work surface, at least one moveable handle and at least one stationary handle, a vertical lift column, a chassis supported on a pair of front caster wheels and a pair of rear caster wheels, and a steering assist system. The steering assist system may include an activation mechanism, an actuation mechanism, and a stopping mechanism. The activation mechanism may be configured to automatically activate the actuation mechanism to move the stopping mechanism from a first position to a second position, thereby preventing or impeding rotation of at least one of the rear caster wheels. When the stopping mechanism is in the second position, the at least one of the rear caster wheels may be configured to abut the stopping mechanism and remain in a substantially straight orientation with respect to a forward facing direction of the cart.

DETAILED DESCRIPTION

Figure 1:
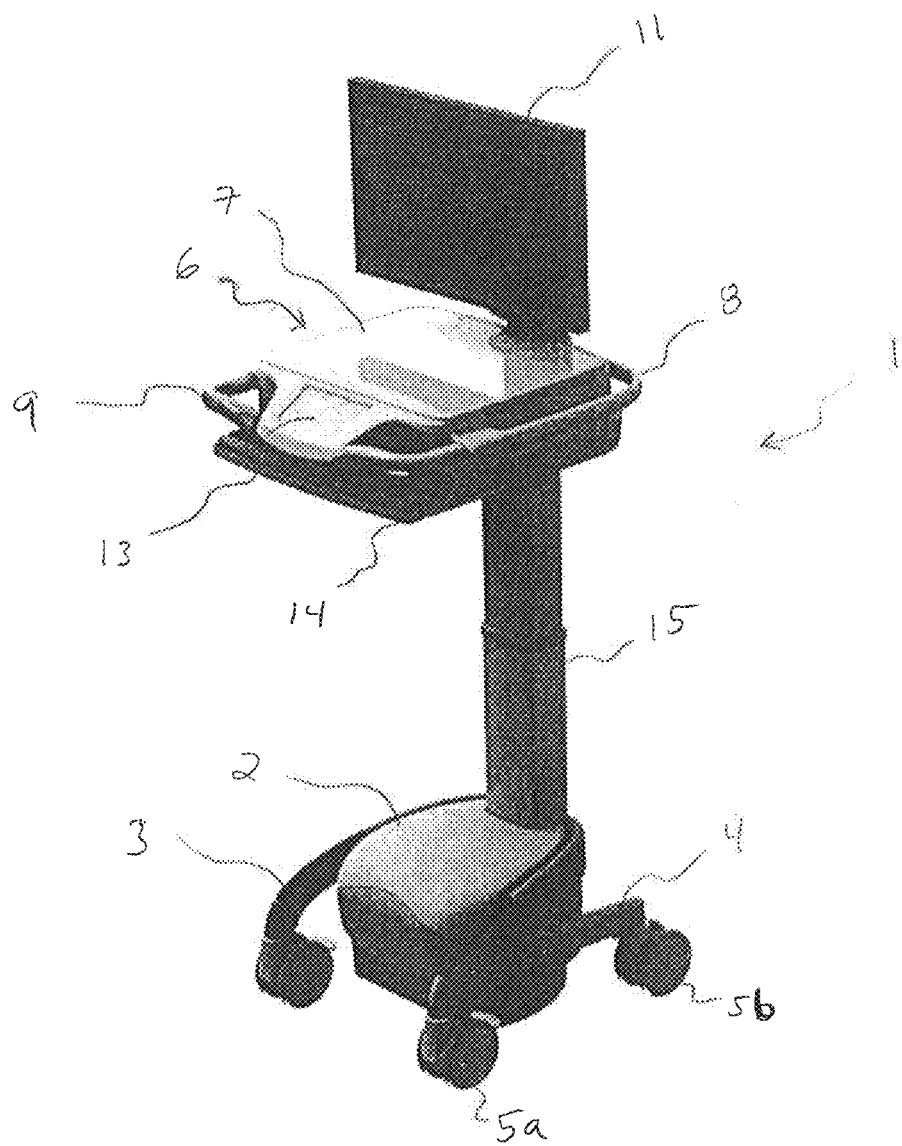
FIG. 1 illustrates a front perspective view of a cart, according to an exemplary disclosed embodiment.
Figure 2:
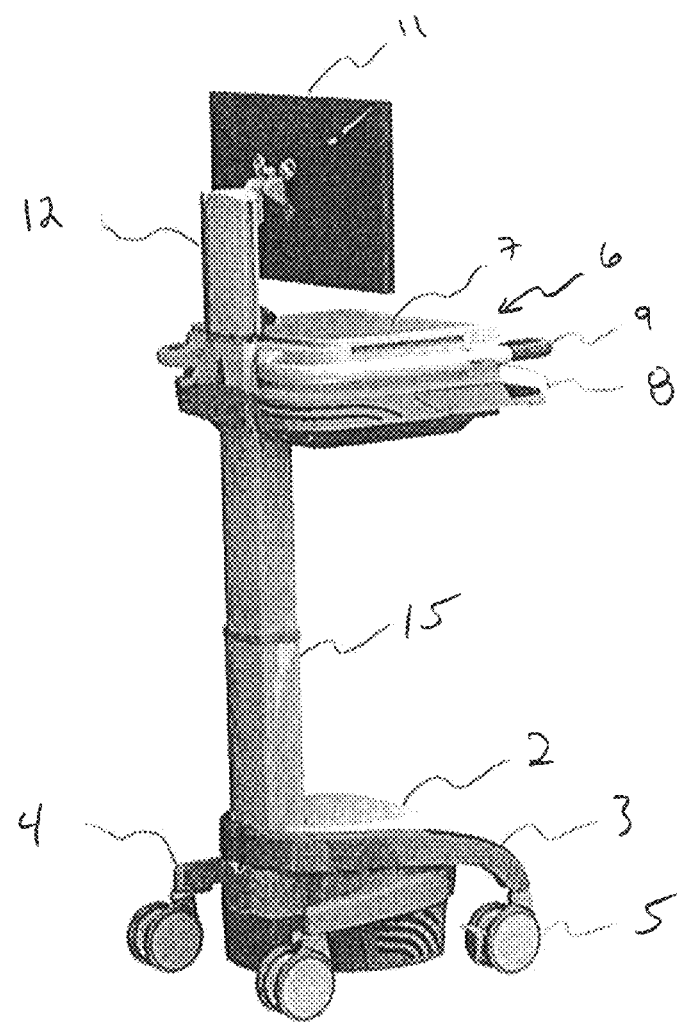
FIG. 2 illustrates a rear perspective view of the cart of FIG. 1.

Reference will now be made in detail to the exemplary embodiments of the present disclosure described above and illustrated in the accompanying drawings. As shown in FIGS. 1 and 2, an exemplary push cart 1—in this case a point-of-care medical cart—may include a chassis or base 2. The chassis 2 may include, for example, upper legs 3 and lower legs 4. Each of the upper and lower legs 3, 4 may be connected to a respective mobility device 5. The mobility devices may be, for example, caster type wheels 5a, 5b that may swivel 360° around a vertical pivot axis, thereby facilitating movement of the cart 1 in all directions.

Figure 3:
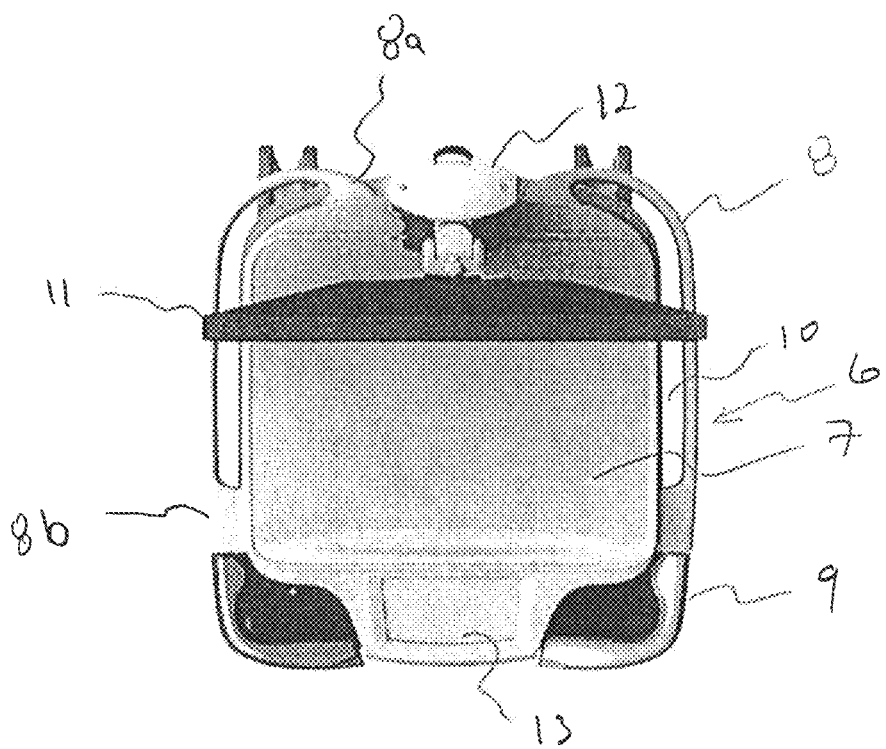
FIG. 3 illustrates a top view of the cart of FIG. 1.

As shown in FIGS. 1-3, the cart 1 may also include a console 6 having a worksurface 7, which may be horizontal and positioned substantially parallel to a floor surface. The worksurface 7 may include a perimeter defined by at least a front edge, a rear edge, and two side edges. Attached to the console 6 may be one or more stationary handles 8, each of which may extend along the perimeter of the worksurface 7, e.g., from an origination point 8a located on the rear edge of the console 6 to a connecting point 8b located on one of the two side edges. In some embodiments, the stationary handle 8 may be connected to the perimeter of the console 6 only at the origination point 8a and the connecting point 8b, such that the stationary handle 8 and the perimeter of the console 6 are separated by a gap 10 extending the length of the stationary handle 8 between the origination point 8a and the connecting point 8b. In other embodiments, the stationary handle 8 may be connected to the console 6 at multiple intermediate positions, or continuously (i.e., without a gap between the console 6 and the stationary handle 8) along the perimeter of the console 6, e.g., so as to form a bulbous rim around the perimeter of the console 6 or worksurface 7. The gap 10 between the stationary handle 8 and the perimeter of the console 6 may be sized to allow a user's hand to move freely therethrough. The cross-section of the stationary handle 8 may be oval or another ergonomic shape, and may have a cross-section that varies along its length.

The console 6 may also include one or more moveable handles 9 axially coupled to the console 6 at a respective connecting point and extending along the perimeter of the horizontal worksurface 7 from the connecting point to an end point located on the front edge of the console 6. Each of the moveable handles 9 may include a connecting device (as set forth in co-pending 62/119,258, which is incorporated by reference in its entirety), which couples the moveable handle 9 to the stationary handle 8 at the connecting point 8b and controls the angular position of the moveable handle 9 relative to the stationary handle 8.

As shown in FIGS. 1 and 2, the cart 1 may also include an adjustable display screen 11 mounted above the console 6. The display screen 11 may be pivotally connected to an adjustable display screen column 12, which may move to vary the vertical position of the display screen 11. The cart 1 may also include a computing device (not shown) mounted in the console 6 below the worksurface 7. The cart 1 may also include a control panel 13. The control panel 13 may be, for example, a touchscreen (e.g., an LCD screen) that is integrated into a projecting portion of the console 6 in front of the worksurface 7 and allows a user to control the computing device and/or other components of the cart 1. The cart 1 may also include an input device tray 14, such as a keyboard and/or mouse tray, located below the control panel 13. The cart 1 may also include a vertical lift column 15 connecting the console 6 to the chassis 2. Although not shown, the chassis 2 may include a power supply (e.g., a rechargeable battery) for supplying power to the cart 1.

Figure 4:
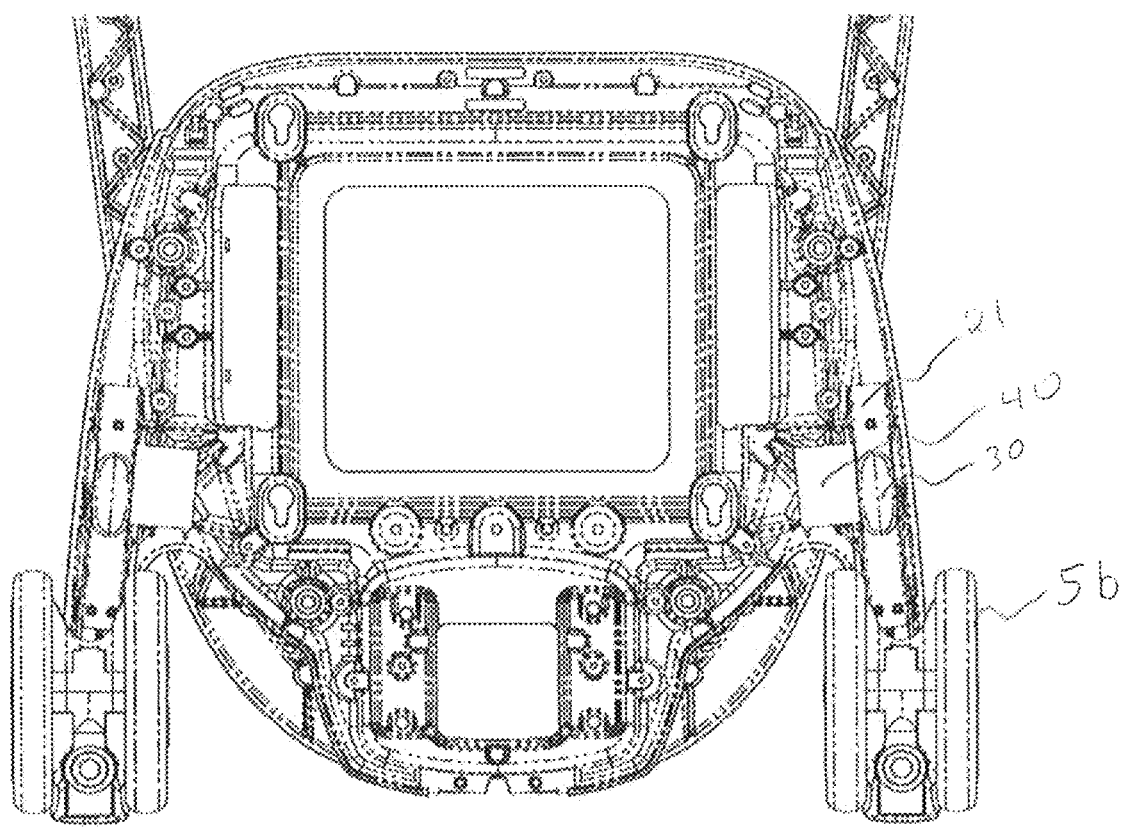
FIG. 4 illustrates a bottom view of the cart of FIG. 1.
Figure 5:
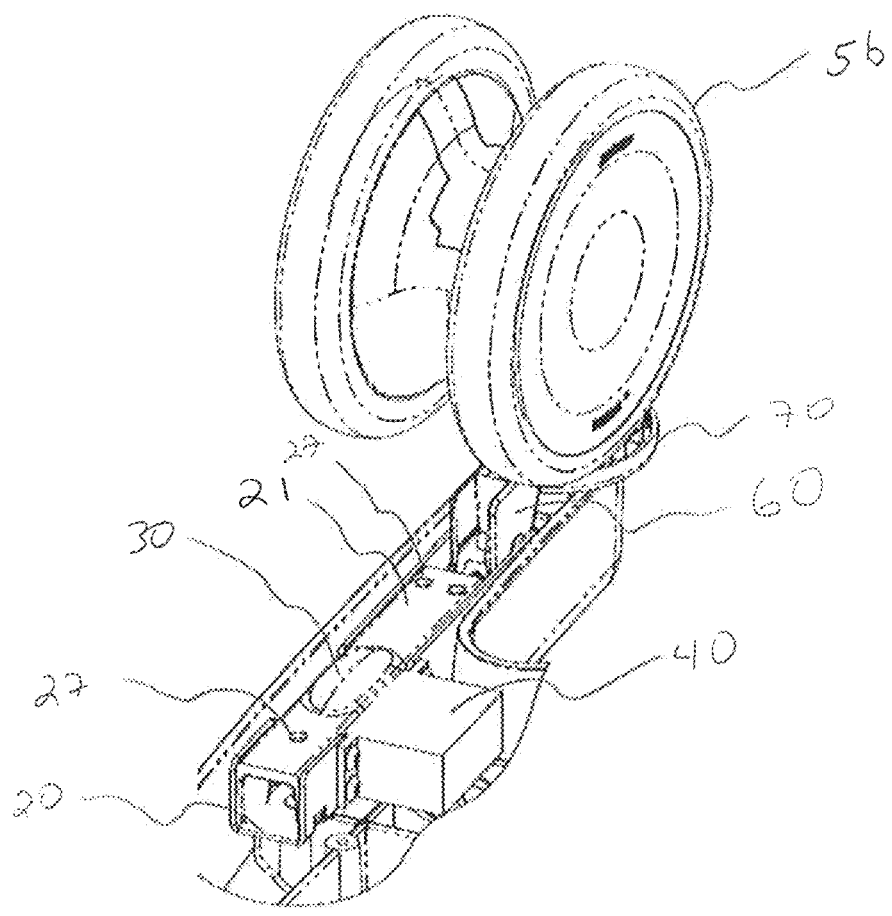
FIG. 5 illustrates a partial perspective view of a steering assist system for the cart of FIG. 1, according to an exemplary disclosed embodiment.

The cart 1 may also include various controllers (not shown), each of which may be in communication with the computing device. For example, the cart 1 may include a controller that is configured to adjust a height of the vertical lift column 15 such that the height of the console 6 may be adjusted to a desired position. Alternatively, the cart 1 may include a primary cart controller that communicates with the computing device and a plurality of secondary controllers, each of which may be in communication with the primary cart controller. The cart 1 may also include a SAS, components of which may be attached to an underside of the chassis 2 (as shown in FIG. 4) to assist the user with steering and controlling the cart 1. One of the various controllers, e.g., the primary cart controller or a secondary controller, may function to activate and deactivate the SAS as will be explained in more detail below.

In some embodiments, the SAS may include multiple mechanisms that collectively comprise the SAS. For example, the SAS may include a support mechanism that supports certain components of the SAS and couples certain components of the SAS to the cart 1. The SAS may also include an activation mechanism that activates certain components of the SAS to provide steering and controlling assistance. The SAS may also include an actuation mechanism that may be controlled by the activation mechanism to provide steering and controlling assistance. The SAS may also include a linkage mechanism that may be actuated by the actuation mechanism to provide steering and controlling assistance. The SAS may also include a stopping mechanism that may be actuated by the actuation mechanism and/or linkage mechanism to provide steering and controlling assistance. The SAS may also include an engagement mechanism that may be engaged or stopped by the stopping mechanism to provide steering and controlling assistance.

Operation of the SAS may include, for example, activation and deactivation of the actuation mechanism by the activation mechanism, which may cause the linkage mechanism to move as desired. Movement of the linkage mechanism may cause the stopping mechanism to continuously move between a first, fully activated position and a second, fully deactivated position. In the fully deactivated position, the engagement mechanism allows the caster wheels 5b to swivel in all directions. Thus, the caster wheels 5b are free to swivel without any assistance when the engagement mechanism is in the fully deactivated position. When in the fully activated position, however, the stopping mechanism may stop or engage the engagement mechanism. When engaged, the engagement mechanism may impede or prevent the caster wheels 5b (i.e., the left and right rear caster wheels) from swiveling past a certain point with respect to the vertical, pivot axis. When the engagement mechanism is engaged by the stopping mechanism, the corresponding caster wheel may be said to be "assisted." Accordingly, assisted caster wheel(s) may facilitate movement for a user who is moving or attempting to move the medial cart 1, as the caster wheel(s) may be maintained in a desired orientation.

For example, as shown in FIGS. 1 and 2, the cart 1 may have four caster wheels 5, two located in a front (5a) of the cart 1 and two located in a rear (5b) of the cart 1. The caster wheels 5b in the rear of the cart 1 may each be configured to cooperate with a support mechanism, actuation mechanism, linkage mechanism, stopping mechanism, and engagement mechanism. In certain embodiments, the cart 1 may include a single activation mechanism that activates the actuation mechanisms for both rear caster wheels 5b. The activation mechanism may be configured to control the steering assistance provided to the left and right caster wheels 5b independently, such that either or both of the left and right rear caster wheels 5b may be locked into a desired orientation. This may be particularly useful when making certain maneuvers that only require steering assistance for one of the rear caster wheels 5b. in other embodiments, however, each caster wheel 5b may have its own corresponding activation mechanism. In such embodiments, the number of assisted caster wheels 5b may equal the number of activation mechanisms. Of course, those skilled in the art will appreciate that the number of caster wheels 5b and activation mechanisms may vary. Once the activation mechanism is activated to control the actuation mechanism for each caster wheel, the rear caster wheels 5b may be prevented or impeded from swiveling in a certain direction. However, even when the rear caster wheels 5b are prevented from swiveling (i.e., they are assisted), the front caster wheels 5a may still be free to swivel 360°. Thus, a user moving the cart 1 may steer the cart 1 more easily to its desired location by swiveling the front wheels 5a while the rear wheels 5b may be assisted by the SAS to remain in a desired orientation (e.g., a straight direction).

Figure 8:
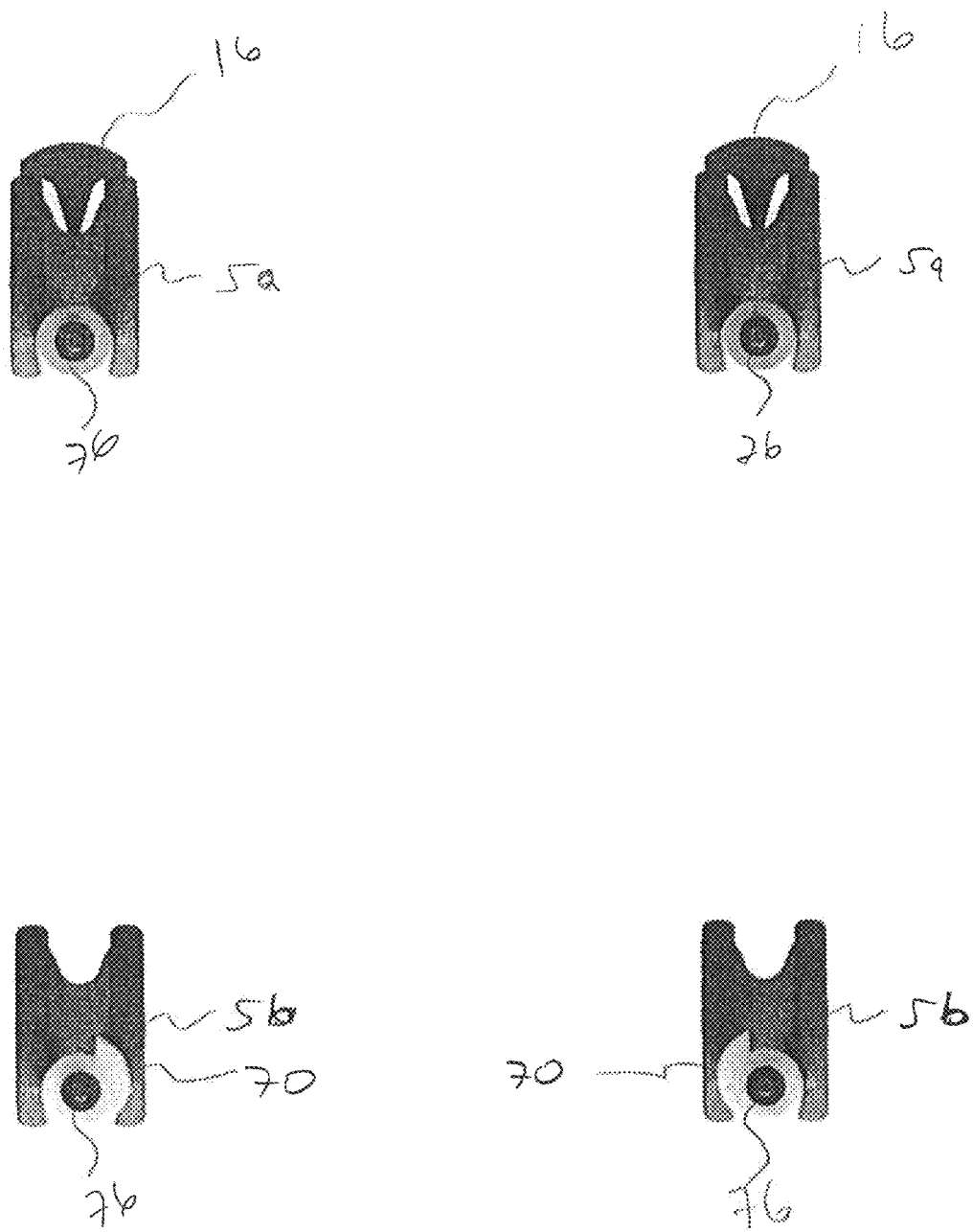
FIG. 8 illustrates a top view of front left, front right, ear left, and rear right caster wheels, according to an exemplary disclosed embodiment.

By way of example, the details of which will be explained further below, the rear caster wheels 5b may both be prevented from swiveling inward toward the center of the cart 1. The engagement mechanism may operate to stop the rear casters from swiveling once they move to a position such that they are substantially parallel with each other and parallel with a path of travel (as shown in FIG. 8). In such a configuration, the front wheels 5a may swivel freely to effect the desired steering and control as a user pushes the cart 1 to its desired location, while the rear caster wheels 5b may be assisted to remain relatively "straight," so as to provide leverage for the user to steer the cart. That is, once the cart 1 twists or turns away from a straight path of travel, the rear caster wheel 5b being turned may be assisted by the SAS such that the SAS may keep that wheel 5b (and thus the cart 1) straight.

The details of the SAS will now be described with reference to FIGS. 1-13. Although the SAS will be described with respect to a single support mechanism, actuation mechanism, linkage mechanism, stopping mechanism, and engagement mechanism, it should be appreciated that the mechanisms configured for use with one of the rear caster wheels 5b may mirror those on the other caster wheel. Alternatively, the left and right rear caster wheels 5b may comprise different mechanisms of the SAS. Further, in embodiments with two or more activation mechanisms (i.e., one for each assisted caster wheel), it should be appreciated that the activation mechanisms may be the same or may be different.

As discussed above, and shown for example in FIGS. 5 and 6, the SAS may include a support mechanism. The support mechanism may include, for example, a frame element 20. The frame element 20 may be configured to support the actuation mechanism, linkage mechanism, and/or the stopping mechanism. For example, the frame element 20 may comprise a U-shaped channel. At one end of the frame element 20, there may be a cutout or opening 22 in the left and right sides of the channel. The actuation mechanism may be configured to be positioned in one of the cutouts 22 such that it may be coupled to and supported by the frame element 20. The stopping mechanism may be configured to be positioned at the other end of the frame element 20, such that it is positioned within the left and right sides of the channel. The linkage mechanism may likewise be configured to be positioned between the actuation mechanism and the stopping mechanism and positioned within the left and right sides of the channel.

Figure 9A:
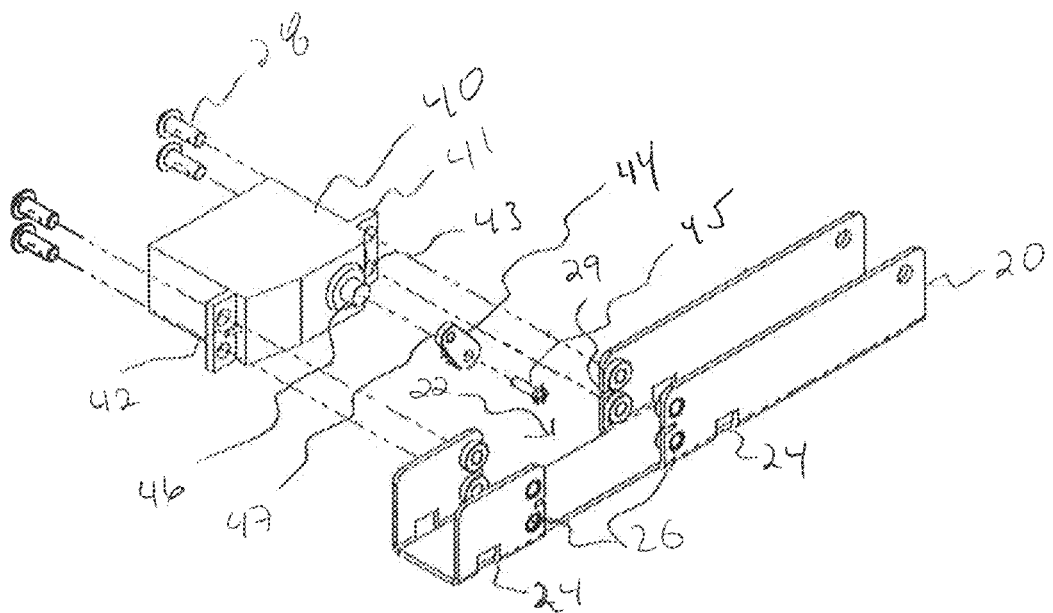
FIGS. 9A and 9B illustrate an exploded and perspective view of a support mechanism and an actuation mechanism of the steering assist system of FIG. 5.
Figure 9B:
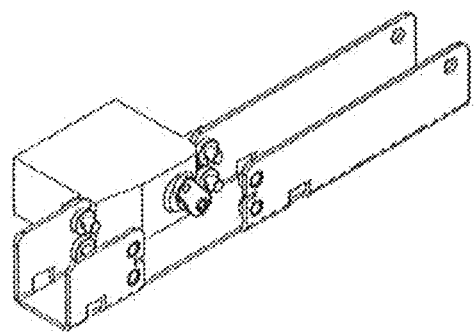
Figure 10A:
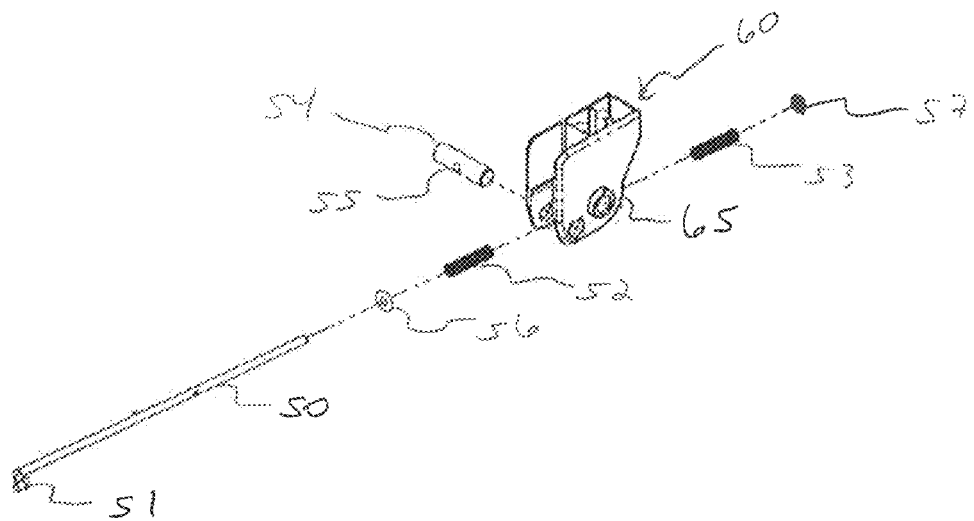
FIGS. 10A and 10B illustrate an exploded and perspective view of a linkage mechanism and a stopping mechanism of the steering assist system of FIG. 5.
Figure 10B:
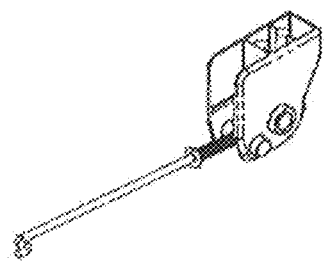
Figure 11A:
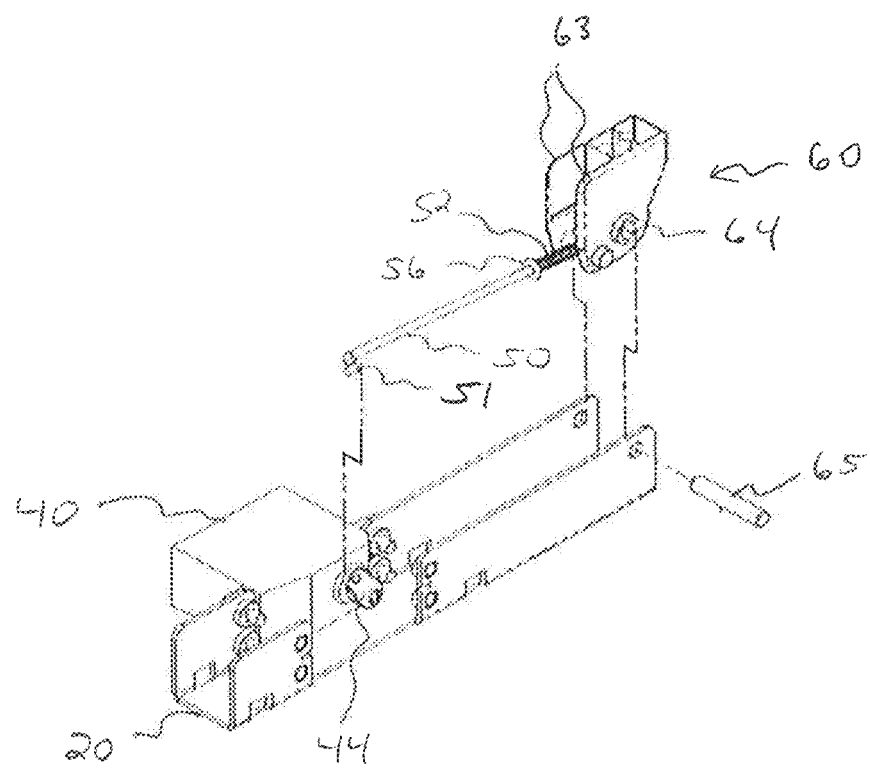
FIGS. 11A and 11B illustrate an exploded and perspective view of a support mechanism, an actuation mechanism, a linkage mechanism, and a stopping mechanism of the steering assist system of FIG. 5.
Figure 11B:
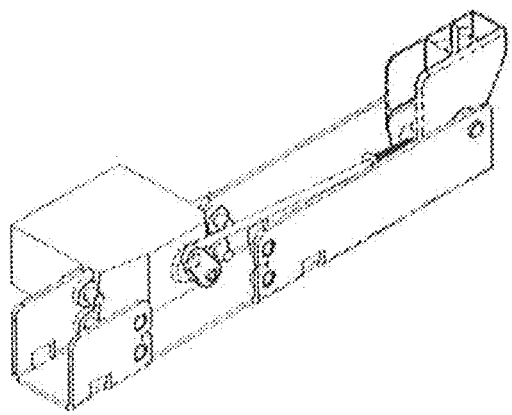

The frame element 20 may include a plurality of fastener-receiving elements, which may be holes 26. As shown in FIGS. 9A and 9B, there may be four holes 26 in each of the left and right sides of the channel. Four of the holes 26 may be located on one end of the channel. On one side of the channel, four of the holes 26 may be adapted to receive fasteners for attaching the actuation mechanism to the frame element 20. On the other side of the channel, four of the holes 26 may also be adapted to receive fasteners for attaching the frame element 20 to the chassis 2 of the cart 1. The two sets of four holes 26 may be substantially aligned, so that the actuation mechanism may be adapted to be attached to either side of the frame element 20 while the other side of the frame element 20 may be attached to the chassis 2 of the cart 1, thereby providing greater flexibility for assembly. As understood for example from viewing FIG. 6, the frame element 20 may also include a plurality of holes 26 in the bottom side of the channel. There may be three holes 26, for example, which may also be used to secure the frame element 20 to the chassis 2 of the cart 1 with fasteners.

In certain embodiments, the fasteners may be bolts 28. In other embodiments, the fasteners may be, for example, screws. It should be appreciated, however, that other mechanical fasteners may be used (removable or fixed), such as rivets, glue, and/or welding, as known to one of ordinary skill in the art. In other embodiments, for example, the frame element 20 may be integral with either or both of the actuation mechanism and the chassis 2 of the cart 1. In such integral embodiments, fasteners are not required. It should also be appreciated that more or less than four holes may be used (or no holes) to couple the frame element 20 to the actuation mechanism and/or the chassis 2 of the cart 1 using the above-mentioned fasteners.

At an opposite of the frame element 20 (i.e., the end not directly coupled to the actuation mechanism), there may be a pair of holes 26, one in each side of the channel. As shown for example in FIGS. 11A and 11B, the holes 26 may be adapted to receive an element of the stopping mechanism, such as a pivot pin 65, allowing the stopping mechanism to be positioned between and moved within the sides of the channel. The holes 26 may be substantially aligned such that the pivot pin 65 is positioned substantially parallel with respect to a bottom side of the channel.

The frame element 20 may also include a notch 29 in each of the left and right sides of the channel, on one or both sides of each cutout 22. The notches 29 may take different shapes, but as shown for example in FIGS. 9A and 9B, the notches 29 may be horizontal notches 29. Each notch 29 may be adapted to receive a corresponding element (e.g., a ridge 42) on the actuation mechanism. The use of the notch 29 and ridge 42 may allow for easier assembly of the actuation mechanism and the frame element 20, as the notch 29 may tend to hold the actuation mechanism in place while the fasteners are secured in place. The notch 29 and ridge 42 may also allow for a more secure connection between the frame element 20 and the actuation mechanism.

The support mechanism may also include, for example, a frame cover 21. As shown for example in FIG. 6, the frame cover 21 may be, for example, a U-shaped channel that may be adapted to fit over some of the exposed elements within the frame element 20. The frame cover 21 may therefore aid to protect the SAS by reducing the likelihood that dust or debris becomes lodged within the components of the SAS. The frame cover 21 may also reduce the likelihood that moving elements of the SAS become caught on other objects, such as a shoelace or bed sheet. The frame cover 21 may also provide the chassis 2 of the cart 1 with a more aesthetically pleasing appearance.

Figure 6:
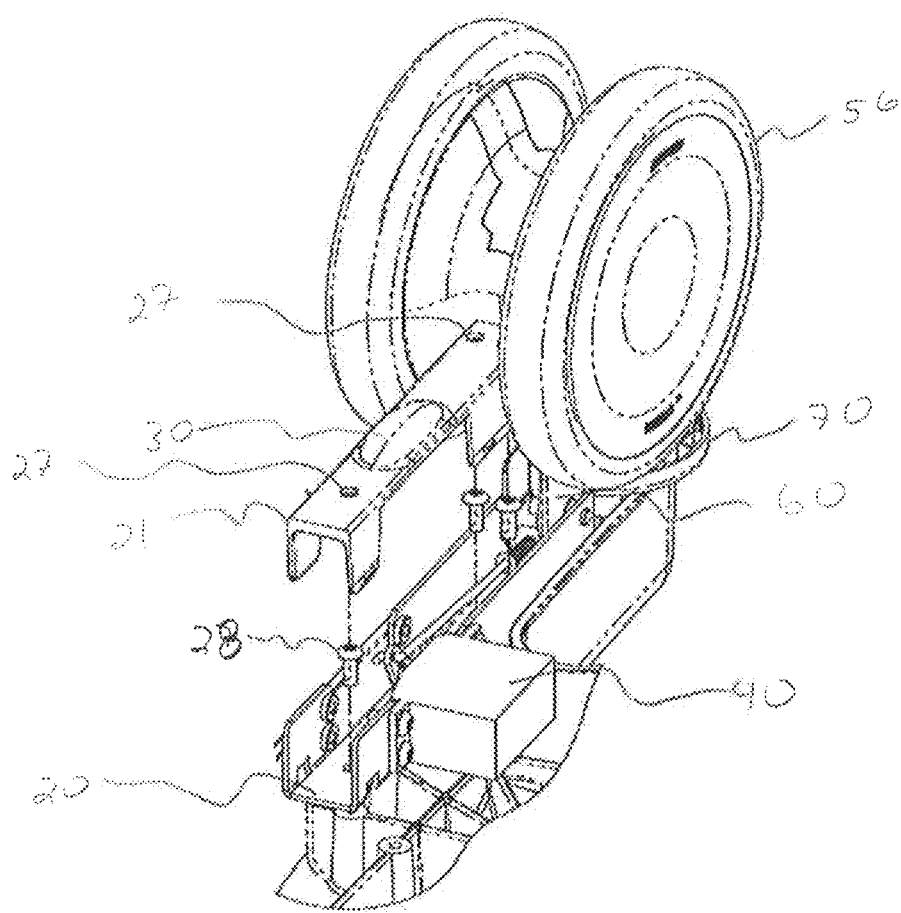
FIG. 6 illustrates a partial exploded view of the steering assist system of FIG. 5, according to an exemplary disclosed embodiment.

As shown for example in FIG. 6, the frame cover 21 may include a pair of cutouts 23 similar in size and/or shape to the cutouts 22 in the frame element 20, thereby allowing the frame cover 21 to be positioned over the frame element 20 and actuation mechanism. The frame cover 21 may be sized such that it covers substantially all of the linkage mechanism. The frame cover 21 may also be sized such that it sits flush with one end of the frame element 20. The frame cover 21 may also be sized such that it does not cover the stopping mechanism. The frame cover 21 may include two sets of attachment elements, one set on each of the left and right sides of the frame cover 21 channel. The attachment elements may be, for example, tabs 25. The tabs 25 may be configured to be received in corresponding tab openings 24 located in the frame element 20. Accordingly, the frame cover 21 may be secured to the frame element 20 using the tabs 25, which may allow for a "snap fit." Alternatively, or in addition to the tabs 25, the frame cover 21 may also include a plurality of fastener receiving elements (e.g., holes 27) adapted to receive a fastener for attaching the frame cover 21 to the frame element 20. In some embodiments, there may be three holes 27 in the bottom side of the U-shaped channel of the frame cover 21 that correspond in size and location to the three holes 26 in the bottom side of the frame element 20 channel. In such embodiments, fasteners may be used to attach the frame cover 21 to the frame element 20 while also attaching both the frame cover 21 and the frame element 20 to the chassis 2 of the cart 1.

The width of the frame cover 21 may be sized such that it fits within the sides of the frame element 20. In some embodiments, the sides of the frame cover 21 may be substantially flush with the sides of the frame element 20 when the frame cover 21 and frame element 20 are secured together. It should also be appreciated that, alternatively, the width of the frame element 20 may be sized such that it fits within the sides of the frame cover 21. It should also be appreciated that the frame element 20 may instead include the tabs 25, while the frame cover 21 includes tab openings 24. Alternatively, the frame element 20 and frame cover 21 may both include tabs 25 and tab openings 24. It should also be appreciated that the frame element 20 and frame cover 21 may be secured together without using the tabs 25 and tab openings 24, and instead may use any of the aforementioned fasteners.

Figure 12A:
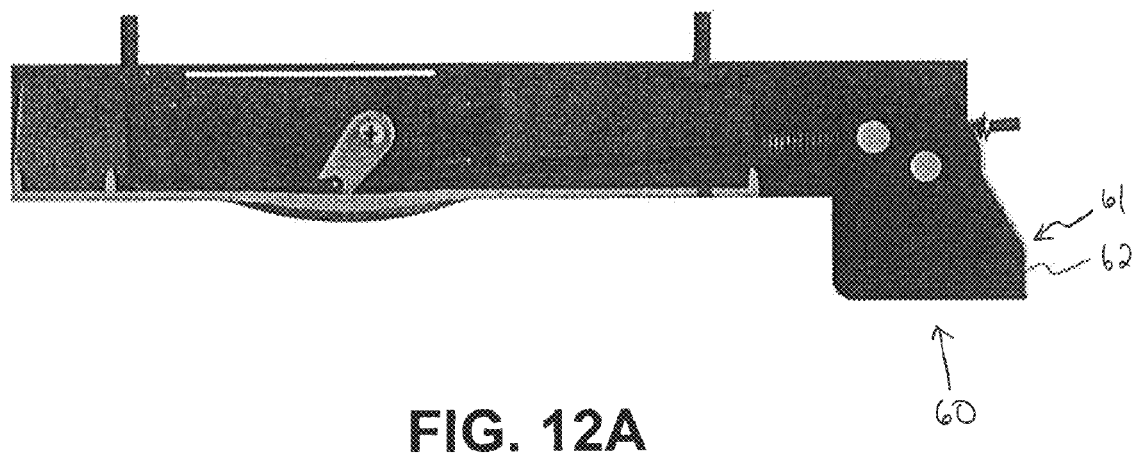
FIGS. 12A and 12B illustrate partial sectional views of the steering assist system of FIG. 5, depicting the stopping mechanism in activated and deactivated positions, respectively.
Figure 12B:
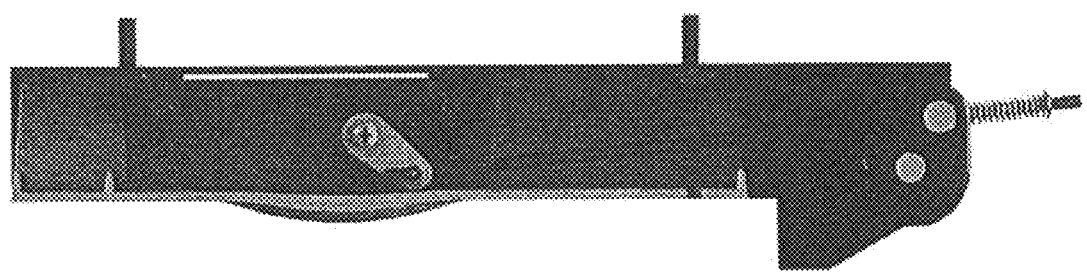
Figure 13A:
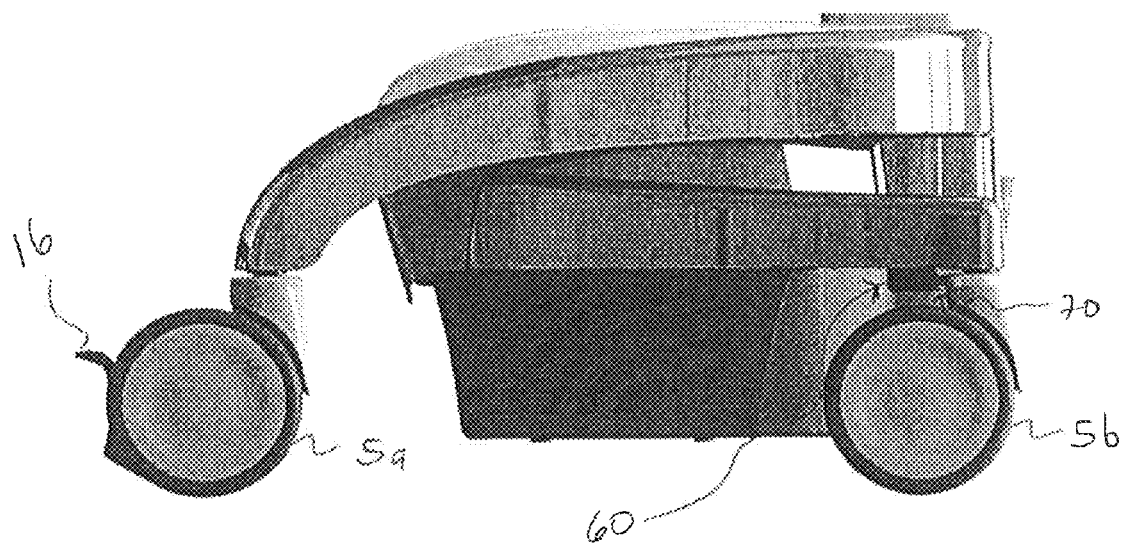
FIGS. 13A and 13B illustrate partial side views of the chassis of the cart of FIG. 1, depicting the stopping mechanism in activated and deactivated positions, respectively.
Figure 13B:
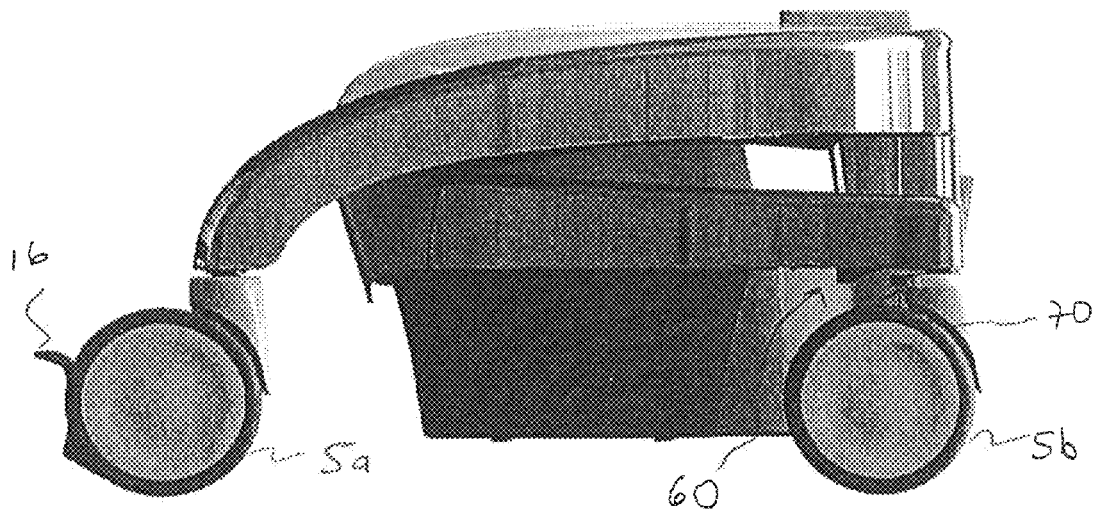

As shown for example in FIGS. 6, 12A, and 12B, the frame cover 21 may also include an extending portion, such as an arcuate protrusion 30. The arcuate protrusion 30 may provide an opening or space for element(s) of the actuation mechanism and linkage mechanism to move within to avoid hitting the frame cover 21. The size and shape of the protrusion 30 in the frame cover 21 may vary, so long as the protrusion 30 provides an appropriate amount of space to allow the element(s) of the actuation mechanism and linkage mechanism to move without being impeded by the frame cover 21. Alternatively, or in addition to the protrusion 30, the frame cover 21 may include a slot, groove, or other opening that may be configured to allow element(s) of the actuation mechanism and linkage mechanism to move within the frame element 20 but without hitting the frame cover 21.

As discussed above, the SAS may include an actuation mechanism. As shown for example in FIGS. 9A, 9B, 11A, and 11B, the actuation mechanism may include, for example, an actuator. The actuator may be an electric motor 40 (e.g., a servo-motor) as known to one of ordinary skill in the art. The electric motor 40 may include, for example, a bracket or flange 41 extending outward on a left and a right side of the electric motor 40. The brackets or flanges 41 may each include a plurality of holes 43. In some embodiments, each bracket or flange 41 may include two holes 43, each of the holes 43 corresponding with one of the holes 26 on one side of the frame element 20 for attaching the electric motor 40 to the frame element 20 using the bolts 28. It should be appreciated that the electric motor 40 may incorporate attachment mechanisms other than a bracket or flange 41 for attaching to the frame element 20.

The electric motor 40 may include a moving member, such as a rotating lever arm 44. The lever arm 44 may be connected to a rotatable output shaft 46 of the electric motor 40 using a screw 45 or other mechanical fastener. The electric motor 40 may thus be adapted to impart a rotational force on the lever arm 44, thereby causing the lever arm 44 to rotate toward or away from the stopping mechanism. As shown in FIGS. 12A and 12B, the lever arm 44 may swing through the protrusion 30 in the frame cover 21 as discussed above. The lever arm 44 may include an attachment element, such as a hole 47. The hole 47 may be configured to attach to an element of the linkage mechanism. As such, rotation of the lever arm 44 may impart a force on the linkage mechanism.

It should be appreciated that the moving member of the actuation mechanism need not be a lever arm 44 and the actuator need not be an electric motor 40, so long as the actuator and moving member may impart a force to the linkage mechanism as needed. Although not shown, in certain embodiments, the lever arm 44 may be replaced with a gear, wheel and axle, screw and nut, and/or other arrangement. Likewise, the electric motor 40 may be replaced with other actuators, such as a solenoid actuator, hydraulic piston, pneumatic actuator, piezoelectric actuator, and/or other actuators.

As discussed above, the SAS may include a linkage mechanism. As shown for example in FIGS. 10A-12B, the linkage mechanism may include multiple components. In one embodiment, the linkage mechanism may include a linkage element, such as a rod or arm 50, which may be configured to sit proximate a center of the frame element 20. The linkage mechanism may also include a connecting element 51 attached to one end of the rod or arm 50. The connecting element 51 may be an L-shaped or S-shaped element, which may be attached to or integral with one end of the rod or arm 50 and configured to fit into the hole 47 in the lever arm 44 of the actuation mechanism. The connecting element 51 may be pivotally attached to the lever arm 44. Through the pivotal attachment to the lever arm 44, the connecting element 51 may receive a force imparted by the lever arm 44, which may cause the rod 50 to move toward or away from the stopping mechanism corresponding with movement of the lever arm 44 toward or away from the stopping mechanism.

One end of the connecting element 51 may be offset a certain distance away from the rod 50 to aid in keeping the connecting element 51 attached to the lever arm 44. The connecting element 51 may also be removably attached to the lever arm 44, which may allow the linkage mechanism to be easily disconnected from the actuation mechanism in the event that either mechanism needs to be repaired or replaced. It should be appreciated that the connecting element 51 may take other forms and may be attached to the moving member of the actuation mechanism in other ways. For example, the L-shaped or S-shaped connecting element 51 may be replaced with another lever arm 44. In such an embodiment, the lever arm 44 of the linkage mechanism may be fixed at one end to the rod 50 while the other end may be pivotally attached to the lever arm 44 of the actuation mechanism.

The linkage mechanism may also include a pair of resistive elements, a driving element, and a pair of retaining elements. In one embodiment, as shown for example in FIGS. 10A and 10B, the resistive elements may include a first spring 52 and a second spring 53, the driving element may include a drive pin 54, and the retaining elements may be a first retaining washer 56 and a second retaining washer 57. The rod or arm 50 (i.e., the linkage element) may be configured to pass through the pair of resistive elements, the driving element, and the pair of retaining elements. For example, the rod 50 may pass first through the first retaining washer 56, which may be fixedly attached to the rod 50. The rod 50 may then pass through the first spring 52, such that the first spring 52 encircles the rod 50. The rod 50 may then pass through a hole 55 in the drive pin 54. The rod 50 may then pass through the second spring 53, such that the second spring 3 encircles the rod 50. Lastly, the rod 50 may pass through the second retaining washer 57, which may be fixedly attached to the rod 50.

Each of the retaining elements may serve as a stopper for one end of a respective resistive element. The other end of each resistive element may be held captive by the drive pin 54. Accordingly, a diameter of the first retainer washer 56 may be larger than a diameter of the first spring 52 and a diameter of the second retainer washer 57 may be larger than a diameter of the second spring 53 to ensure that the springs may be held captive on the washers 56, 57. Similarly, a diameter of the drive pin 54 may be larger than a diameter of both the first and second springs 52, 53 to provide enough surface area such that the entire end of each of the first and second springs 52, 53 contacts the drive pin 54. Although not shown, it should be appreciated that each of the retaining washers 56, 57 and each side of the drive pin 54 may include a notch or groove (e.g., a circular notch or groove with substantially the same diameter as the first and second springs 52, 53 adapted to receive a respective end of the first and second springs 52, 53. Such a notch or groove may enhance the securement and reduce the potential for slippage between the spring ends and the washers 56, 57 and/or drive pin 54. The retaining elements may also each comprise elements other than washers 56, 57, and may instead be, for example, retaining detents or knob. Alternatively, the rod 50 may include a fattened region or outward projection to serve as a retaining element.

In operation, the activation mechanism may be activated to cause the electric motor 40 to impart a rotating force on the lever arm 44 toward the stopping mechanism. Consequently, the lever arm 44 may rotate towards the stopping mechanism, thereby causing the rod 50 to move toward the stopping mechanism. As the rod 50 moves toward the stopping mechanism, the first retaining washer 56 may cause the first spring 52 to impart a force on the drive pin 54, which may cause the drive pin 54 (and thus the stopping mechanism) to move. In some embodiments, the stopping mechanism may pivot toward and away from the frame element 20, as shown in FIGS. 12A and 12B. As the rod 50 continues to move, the first retaining washer 56 may continue to move to force the spring to move the drive pin 54 (and thus continue to pivot the stopping mechanism), which will also cause the first spring 52 to compress. The electric motor 40 may be controlled such that it stops rotating the lever arm 44 toward the stopping mechanism when the stopping mechanism has reached the fully deactivated position, as shown in FIG. 12B. When the stopping mechanism is in a fully deactivated position, the first spring 52 may be fully compressed. In other embodiments, the first spring 52 may be partially compressed when the stopping mechanism is in a fully deactivated position.

The operation of SAS works similarly when moving the stopping mechanism to a fully activated position, as shown in FIG. 12A. For example, the electric motor 40 may begin rotating the lever arm 44 away from the stopping mechanism (e.g., from the position shown in FIG. 12B to the position shown in FIG. 12A). As the rod 50 moves away from the stopping mechanism, the first retaining washer 56 may allow the first spring 52 to move away from the drive pin 54 such that it decompresses. While the first spring 52 decompresses, the second retaining washer 57 may, for example, cause the second spring 53 to begin compressing as it imparts a force on the drive pin 54, which may cause the drive pin 54 (and thus the stopping mechanism) to pivot away from the frame element 20 and toward an activated position. As the lever arm 44 continues to move away from the stopping mechanism, the first spring 52 may continue to decompress and the second spring 53 may continue to compress. The electric motor 40 may be controlled such that it stops rotating the lever arm 44 away from the stopping mechanism when the stopping mechanism has reached the fully activated position. When the stopping mechanism is in a fully activated position, the second spring 53 may be fully compressed. In other embodiments, the second spring 53 may be partially compressed when the stopping mechanism is in a fully activated position. As understood from the above description and the Figures, the stopping mechanism may be moved through an infinite number of positions between a fully activated position and a fully deactivated position.

As shown for example in FIGS. 10A-12B, the stopping mechanism may include a latch or stop 60. In some embodiments, the latch 60 may comprise two side plates 63 with a channel or opening therebetween. The side plates 63 may each include a pair of openings 64. One opening 64 of each of the pair of openings 64 may be configured to receive a respective end of the stopping mechanism's pivot pin 65 such that the pivot pin 65 may be positioned between each of the side plates 63. As mentioned above, the pivot pin 65 may allow the stopping mechanism to pivot toward and away from the frame element 20. The other opening 64 of each of the pair of openings 64 may be configured to receive a respective end of the linkage mechanism's drive pin 54 such that the drive pin 54 may be positioned between each of the side plates 63. As mentioned above, the drive pin 54 may be moved by the force of the first and/or second spring 53 such that it rotates about the pivot pin 65, thereby allowing the latch 60 to move between activated and deactivated positions.

The latch 60 may include a latching portion 62 with a substantially flat face 62 that is configured to abut the engagement mechanism such that the caster wheel to which the engagement mechanism is attached may be assisted for steering. It should be appreciated that the latching portion 61 may take other shapes, so long as it functions to prevent the caster wheel from swiveling in one direction while allowing the caster wheel to swivel in another direction, as explained in detail below. Further, while the pivot pin 65 may be fixed to the frame element 20 near the frame cover 21 (as shown in FIGS. 12A and 12B), it should be appreciated that the location of the pivot pin 65 on the frame element 20 may be varied (along with the size of the latch 60), so long as the latch 60 does not impede the translational motion of the caster wheels 5b when the latch 60 is in an activated position and does not abut the caster wheel's engagement mechanism when the latch 60 is not in an activated position.

As discussed above, the SAS may include an engagement mechanism. As shown for example in FIGS. 7A and 7B, the engagement mechanism may include a caster cap 70. The caster cap 70 may be fixedly attached to a caster wheel using fasteners known to those skilled in the art. Alternatively, the caster cap 70 may be integral with a caster wheel 5b. The caster cap 70 may include an aperture adapted to receiving a caster wheel pivot 76. Accordingly, the caster cap 70 and the caster wheel 5b may both move in unison 360° about a vertical axis, the vertical axis passing through the center of the caster wheel pivot 76.

In some embodiments, the caster cap 70 may be shaped such that a cross section of the cap resembles a nautilus shell. As shown for example in FIG. 7A, the caster cap 70 may include a top surface 71, a side surface 72, and an intermediate surface 73 located between the top surface 71 and the side surface 72. Although not shown, the caster cap 70 may also include a bottom surface. The side surface 72 of the caster cap 70 may include an engagement portion 74. The engagement portion 74 may be substantially flat (i.e., substantially parallel to the vertical axis of the caster wheel pivot 76). The perimeter of the caster cap 70 may comprise an outer diameter and an inner diameter. The width of the engagement portion 74 may be equal to a difference, between the outer diameter and the inner diameter. The intermediate surface 73 may comprise a ramp or a beveled edge. The intermediate surface 73 of the caster cap 70 may include a disengagement portion 75. A height of the side surface 72 of the caster cap 70 may be substantially equal to a height of the intermediate surface 73.

Figure 7A:
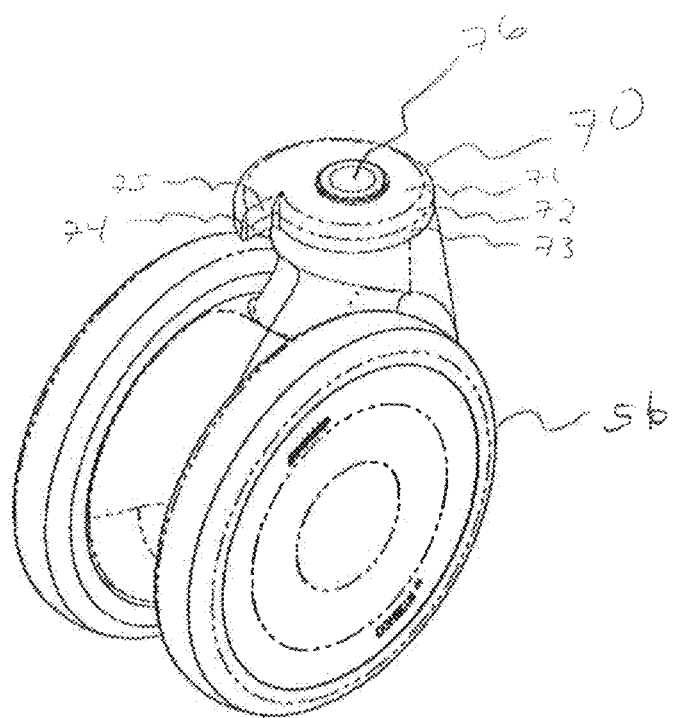
FIG. 7A illustrates a perspective view of a rear caster wheel, according to an exemplary disclosed embodiment.
Figure 7B:
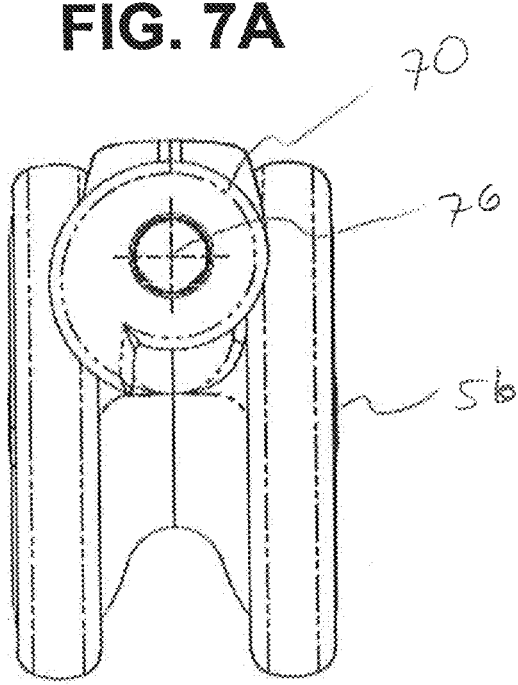
FIG. 7B illustrates a top view of the rear caster wheel of FIG. 7A.

As shown for example in FIG. 7B, the engagement and disengagement portions 74, 75 of the caster cap 70 may be offset from a centerline of the caster cap 70 and caster wheel pivot 76. The offset may be sized such that a horizontal distance from the engagement portion 74 to the centerline of the caster cap 70 and caster wheel pivot 76 is substantially equal to the width of the stopping mechanism's latching portion 61. As such, when the stopping mechanism is in a fully activated position, the caster wheels 5b may swivel in one direction (i.e., the direction that the engagement portion 74 faces) until the engagement portion 74 abuts the latching portion 61 of the stopping mechanism. When this abutment occurs, the caster wheels 5b may be substantially straight (as shown in FIG. 8). That is, the caster wheels 5b may be substantially parallel to the side plates 63 of the stopping mechanism, which are substantially parallel to a forward direction of the cart 1 (the forward direction being orthogonal to the display screen 11). Accordingly, the SAS may cause the caster wheels 5b to remain substantially straight by preventing the caster wheels 5b from swiveling inward if the cart 1 begins to turn or twist, so that it may assist the user in steering and controlling the cart 1.

In one embodiment, for example, the disengagement portion 75 may also comprise a ramp or a beveled edge, and the width of the of disengagement portion 75 may be substantially equal to the width of the engagement portion 74. The disengagement portion 75 may prevent the caster wheels 5*b* from being maintained in a straight position when the stopping mechanism is activated but not fully activated. For example, when the caster wheels 5*b* are swiveled in one direction (i.e., the direction that the disengagement portion 75 faces) and the latching portion 61 of the stopping mechanism is not positioned to abut the engagement portion 74 and only abuts the disengagement portion 75, the caster wheel 5*b* may overcome the downward force of the latching portion 61 and continue swiveling. Because of the shape of the disengagement portion 75 (i.e., its ramp or beveled edge), the caster cap 70 may overcome the force of the second spring 53 to push the stopping mechanism back toward the frame element 20 (i.e., away from the fully activated position) as the disengagement portion 75 slides past the bottom of the stopping mechanism. However, when the stopping mechanism is in a fully activated position, the caster cap 70 may not be able to push the stopping mechanism upward, and the caster wheel 5*b* may be prevented from continued swiveling. Such an arrangement may be advantageous because it may ensure that the caster wheels 5*b* are only maintained in a straight position when the stopping mechanism is fully activated.

The rest of the intermediate surface 73 (i.e., the portion other than the disengagement portion 75) may function similarly to the disengagement portion 75. That is, the beveled edge or ramp of the intermediate surface 73 may allow the caster wheels 5*b* to continue swiveling in one direction (i.e., the direction that the disengagement portion 75 does not face). That is, the shape of the intermediate surface's 73 beveled edge may allow the caster cap 70 to overcome the force of the second spring 53 to push the stopping mechanism back toward the frame element 20 (i.e., away from the fully activated position) when the caster cap 70 is swiveled in the direction that the disengagement portion 75 does not face. In some embodiments, the intermediate surface 73 may be able to overcome the force of the second spring 53 to push the stopping mechanism back toward the frame element 20 when only the intermediate surface 73 abuts the stopping mechanism (i.e., when the stopping mechanism is only partially activated). In other embodiments, however, the intermediate surface 73 may be able to overcome the force of the second spring 53 to push the stopping mechanism back toward the frame element 20 even when the stopping mechanism is fully activated.

It should be appreciated however that the caster cap 70 may not include the disengagement portion 75. In such embodiments, the surface of the caster cap 70 that would otherwise be the disengagement portion 75 may also be substantially flat, such that the engagement portion 74 may be twice as large in embodiments without a disengagement portion 75. It should also be appreciated that the caster cap 70 may include engagement and disengagement portions 74, 75 that are not substantially equal in size. Further, for example, the caster cap 70 may comprise shapes other than a nautilus shell shape.

It should also be appreciated that the stiffness of the second spring 53 may be selected such that the caster cap 70 (through the intermediate surface 73) cannot overcome the force of the second spring 53 to push the stopping mechanism back toward the frame element 20 without great difficulty. Conversely, the stiffness of the second spring 53 may be selected such that the caster cap 70 may easily overcome the force of the second spring 53. It should be appreciated however that the stiffness of each of the first and second springs 52, 53 may be selected such that the force imparted by the actuation mechanism is greater than the force required to move the drive pin 54 and consequently pivot the stopping mechanism between the fully activate and fully deactivated positions. In other words, the resistance of the first and second springs 52, 53 may be selected so that the electric motor 40 can overcome the force of the springs to move the stopping mechanism toward and away from the frame element 20.

As discussed above, the SAS may include an activation mechanism. In one embodiment, for example, the activation mechanism may be fully automated (i.e., it does not require user activation) so it may activate and deactivate the steering assistance on-the-fly. For example, the cart 1 may comprise an activation mechanism controller (not shown) that communicates with the computing device and/or primary cart controller and one or more data measuring devices (not shown). When the data measuring device provides an indication to the controller that steering assistance is needed or no longer needed, the activation mechanism controller may activate the actuation mechanism to effectuate movement of the stopping mechanism as described above.

In one embodiment, for example, one of the data measuring devices may be an accelerometer (not shown). The accelerometer may be located, for example, in the console 6 or in other components of the cart 1, such as the stationary handles or the chassis 2. The accelerometer may sense, for example, that the cart 1 is moving in a specified direction (e.g., straight forward), or at or above a certain rate, or that the cart 1 has begun moving from a stationary position. Based on the direction or rate of movement, the accelerometer may then indicate to the activation mechanism controller that steering assistance is needed. Conversely, the accelerometer may sense that the cart 1 is moving in a certain direction (e.g., sideways) or at or below a certain rate (or is stationary) and may indicate to the activation mechanism controller that steering assistance is no longer needed. It should be appreciated that the accelerometer may be used in other various ways to communicate to the activation mechanism controller that steering assistance is needed or no longer needed, such as when the cart 1 is moving in directions other than straight or sideways and/or when the acceleration or deceleration of the cart 1 is above and/or below a threshold value.

In one embodiment, for example, one of the data measuring devices may be a gauge (such as, for example, a force or strain gauge). The gauge (not shown) may be located, for example, in one or both of moveable push handles 9 (or in other components of the cart 1, such as stationary handles). The gauge may be configured to indicate to the activation mechanism controller that steering assistance is needed or no longer needed depending on the amount of strain or force measured in the handles. For example, when a user begins to push the cart 1 from a stopped position (or when a user attempts to steer and/or control the cart 1), the gauge may measure a strain or force above a threshold value. As another example, the gauge may sense and/or measure a difference in strain on the two movable handles 9 (or two stationary handles) indicative of the user attempting to steer the cart in a new direction. When this occurs, the gauge may indicate that steering assistance is needed. Conversely, when the gauge measures a strain force at or below a threshold value, the gauge may indicate that steering assistance is not needed. Of course, steering assistance may be desired even when the measured force or strain is at or below a threshold value, such as when the cart 1 is already moving and the momentum of the cart 1 requires the user to impart very little force or strain on the handles. Accordingly, the controller may be configured such that the gauge may only communicate that activation of the actuation mechanism is required. That is, when the strain or force is at or below a threshold value, the steering assistance will not be deactivated. It should be appreciated that other data measuring devices may be incorporated into the cart 1, and the disclosure is not limited to the accelerometer or gauges described above.

In another embodiment, for example, one of the data measuring devices may be a detent switch (such as, for example, a push button switch) that senses rotation of the movable push handles 9. The detent (not shown) may be located, for example, so as to sense rotation of the one or both of moveable handles 9 toward the outside of the cart. In one embodiment, the detent may be configured to indicate when the movable handle has reached the limit of its rotation to the outside of the cart 1, indicating that the user wishes to steer the cart in that direction. When this occurs, the detent may indicate that steering assistance is needed. Conversely, when the movable handles are rotated back toward the center of the cart, the detent may indicate that steering assistance is no longer needed.

The activation mechanism may also comprise other mechanisms for activating and deactivating the actuation mechanism. For example, the activation mechanism may comprise a real-time location system (such as a global positioning system or other location system) that is configured to indicate to the activation mechanism controller that steering assistance is needed or no longer needed depending on the location of the cart 1. The real-time location system may include a Global Positioning System (GPS) device or another location device. For example, the real-time location device may be implemented by a wireless tracking device on the cart 1 that may to locate the cart 1, e.g., by triangulating or detecting the strength of wireless signals, and continuously feeds location information to the activation mechanism controller. The GPS device or tracking device (not shown) may be located, for example, in the console 6 or in other components of the cart 1, such as the chassis 2. If the real-time location system signals to the controller that the cart 1 is located, e.g., in the middle of a hospital corridor (a location where steering assistance is likely to be desired because the cart 1 may need to be pushed straight forward), the controller may be configured to activate the actuation mechanism to provide steering assistance. Further, if the real-time location system signals to the controller that the cart 1 is located, e.g., in an operating room, the controller may be configured to deactivate the actuation mechanism to no longer provide steering assistance.

It is also envisioned that a user may input information to the computing device about a health-care environment in which the cart 1 may be used to further assist the activation mechanism. For example, a hospital layout may be received by the computing device, and a user may choose where in the hospital the steering assistance should be activated or deactivated. As the user moves the cart 1 around the hospital, the real-time location system may then indicate to the controller whether steering assistance is needed depending on the user-selected locations. Accordingly, steering assistance may be personalized to fit each individual user's needs and/or each health-care environments needs, as desired.

The activation mechanism may also comprise, for example, a voice-activation system. The voice-activation system may be configured such that when certain commands are given, the voice-activation system may indicate to the activation mechanism controller that steering assistance is needed or no longer needed. The voice-activation system (not shown) may be located, for example, in the console 6 or in other components of the cart 1. As a user begins to move the cart 1 down a hospital hallway, e.g., the user may say "steering assist on," which may cause the activation mechanism controller to activate the actuation mechanism to provide steering assistance. Conversely, for example, as a user begins to move the cart 1 sideways, the user may say "steering assist off," which may cause the activation mechanism controller to deactivate the actuation mechanism to no longer provide steering assistance. The voice-activation system may be configured such that it only responds under certain circumstances. For example, a user may be forced to enter a password into the computing device before the voice-activation system will work. Alternatively, or in addition to the password protection, the voice-activation system may be configured such that it has voice recognition and only responds to certain voices (e.g., health-care providers). Using such safety measures may prevent the voice-activation system from being triggered accidentally, unintentionally, or by someone without authority.

The activation mechanism may also comprise, for example, a push button. The push button (not shown) may be located, for example, on the touchscreen of the control panel 13. The push button may be configured such that a user may manually press the button to activate or deactivate the steering assistance as desired. The push button may be located elsewhere on the cart 1, such as on the stationary or adjustable handles. While it is desirable to incorporate a fully automated activation mechanism to increase user productivity and/or to avoid misuse that may occur because of user activation, the manual push button may serve as a failsafe in the event that the other components of the activation mechanism are not responding. In some embodiments, however, the push button may be the only way to activate or deactivate the steering assistance.

The cart 1 may also comprise a visual indicator (not shown) that may indicate when the steering assistance is on or off. For example, the control panel 13 may include a light (e.g., an LED) that turns on when the steering assistance is activated and turns off when the steering assistance is deactivated. The visual indicator may be located elsewhere on the cart 1, such as on the stationary or adjustable handles or on the monitor.

The cart 1 may also comprise an audible indicator (not shown) that may indicate when the steering assistance is on or off. For example, the control panel 13 may include a noise-produce mechanism that emits a first sound (e.g., a beep or ping) when the steering assistance is activated and emits a second sound (e.g., two beeps or pings) when the steering assistance is deactivated. The audible indicator may also use a voice that says "on" or "off." The audible indicator may be located elsewhere on the cart 1, such as on the stationary or adjustable handles or on the monitor, and may also produce other sounds.

The cart 1 may also comprise a tactile indicator (not shown) that may indicate when the steering assistance is on or off. For example, the movable handles 9 may be equipped with a vibratory motor or other tactile indicator that indicates when the steering assistance is activated or deactivated.

It should also be appreciated that any of the data measuring devices may be used in conjunction with one another and/or may be used in conjunction with the real-time location system, voice-activation system, and/or push button. For example, a gauge may be used to indicate to the controller that steering assistance is needed while the accelerometer may be used to indicate to the controller that steering assistance is not needed. Likewise, the real-time location system may be used to indicate to the controller that steering assistance is needed while the voice-activation system may be used to indicate to the controller that steering assistance is not needed. Further, for example, the real-time location system may be used to signal to the controller that the cart 1 is located outside of a patient's room and one or more of the data measuring devices may simultaneously sense that steering assistance is needed (e.g., because the accelerometer senses that the cart 1 is trying to be turned), thereby causing the controller to activate or deactivate the actuation mechanism to provide or remove steering assistance.

The cart 1 may also comprise, for example, one or more caster wheel locking mechanisms. As shown in FIGS. 1 and 8, for example, each of the front caster wheels 5a may comprise a foot paddle or tab 16 that extends outward from the wheel, which may be moved by a user to lock or unlock the wheels using a locking mechanism (not shown) on each wheel. Accordingly, the caster wheel locking mechanisms may prevent unintended movement once the cart 1 has been moved to a desired location. Such locking mechanisms may be, for example, a simple wedge, brake, or clamp, as known to those of ordinary skill in the art.

Operation of one embodiment of the cart 1 will now be described with respect to the SAS. When a user desires to move the medical from one location to another (e.g., from one patient's room to another), the user may grasp one or both of the adjustable handles and begin pushing the cart 1 in the desired direction while the stopping mechanism is in a fully deactivated position (i.e., the position shown in FIG. 12B). As the user moves the cart 1 toward its desired location, the momentum of the cart 1 may tend to continue movement of the cart in an undesired direction (e.g., continuing straight forward instead of around a corner). At this point, the activation mechanism may be activated (in any of the manners discussed above) such that the activation mechanism controller activates the actuation mechanism on each of the left and right caster wheels 5b. As described above, the actuation mechanisms may then rotate the lever arms 44 to move the rod of each linkage mechanism, which may cause the stopping mechanisms to move to a fully activated position (i.e., the position shown in FIG. 12A).

As shown in FIG. 8, the caster cap 70 for the left rear caster wheel 5b is "flipped" compared to the caster cap 70 for the right rear caster wheel 5b. FIG. 8 depicts an arrangement of all four caster wheels 5a, 5b being in a straight orientation. The upper left and right wheels correspond to the front right and left caster wheels 5a, respectively. The lower left and right wheels correspond to the rear right and left caster wheels 5b, respectively. As the user pushes the cart 1 forward, each of the left and right rear caster wheels 5b will tend to swivel inward toward the vertical lift column 15. Accordingly, as the cart 1 is pushed forward, the left rear caster wheel 5b may swivel inward and clockwise (when viewed from the top as in FIG. 8), causing its caster cap 70 to swivel until it engages the corresponding stopping mechanism. Likewise, the right rear caster wheel 5b may swivel inward and counterclockwise (again, when viewed from the top as in FIG. 8), causing its caster cap 70 to swivel until it engages the corresponding stopping mechanism. Thus, even if the left and right rear caster wheels 5b are initially out of synchronization (i.e., in different orientations with respect a vertical axis), both will eventually be stopped in a straight orientation (as shown in FIG. 8) when their respective stopping mechanisms are fully activated, as shown for example in FIG. 13A. However, as described above, if the left and right rear caster wheels 5b swivel outward (i.e., away from the vertical lift column 15), they may contact their respective stopping mechanisms and then continue to swivel outward after sliding past the stopping mechanisms (due to the beveled edge or ramp on the intermediate surface 73 of each caster cap 70, as described above).

Once the left and right rear caster wheels 5b are in a straight orientation (i.e., both are assisted), the user is better able to steer and control the cart 1 by leveraging the front of the cart 1 around the rear wheels, so that the user may move the cart 1 to a desired location. When the user reaches the desired location (or while moving toward the desired location), the activation mechanism controller may deactivate the actuation mechanism (in any of the manners discussed above) on each of the left and right caster wheels 5b, thereby moving the stopping mechanisms to a fully deactivated position, as shown for example in FIG. 13B. The left and right rear caster wheels 5b may then be able to freely swivel 360° without being impeded or prevented from moving by their respective stopping mechanisms, so that the user may maneuver the cart to its final desired location.

Because numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. A steering assist system for a cart having a plurality of wheels, the steering assist system comprising:
   an activation mechanism;
   a first actuation mechanism;
   a first support mechanism;
   a first linkage mechanism;
   a first stopping mechanism; and
   a first engagement mechanism including a caster cap having a ramp and an engagement portion, and wherein the ramp and the engagement portion are configured to contact the first stopping mechanism, the first stopping mechanism is configured to abut the first engagement mechanism to impede rotational movement of at least one of the plurality of wheels, and the activation mechanism is configured to activate the first actuation mechanism, causing the first linkage mechanism and the first stopping mechanism to move.

2. The steering assist system of claim 1, wherein the first actuation mechanism is connected to the first linkage mechanism and the first linkage mechanism is connected to the first stopping mechanism.

3. The steering assist system of claim 1, wherein the first stopping mechanism is configured to move between a fully activated position and a fully deactivated position.

4. The steering assist system of claim 3, wherein when the first stopping mechanism is in the fully activated position, the first stopping mechanism is configured to abut the first engagement mechanism to impede rotational movement of the at least one of the plurality of wheels.

5. The steering assist system of claim 1, including:
   a second actuation mechanism;
   a second support mechanism;
   a second linkage mechanism;
   a second stopping mechanism; and
   a second engagement mechanism, wherein the second stopping mechanism is configured to abut the second engagement mechanism to impede rotational movement of at least a second one of the plurality of wheels.

6. The steering assist system of claim 1, wherein the activation mechanism includes at least one of: a data measuring device, a real-time location system, a voice-activation system, and a push button.

7. The steering assist system of claim 1, wherein the first actuation mechanism includes an electric motor and a lever arm.

8. The steering assist system of claim 1, wherein the first linkage mechanism includes a rod, at least one resistive element, a driving element, and at least one retaining element.

9. The steering assist system of claim 1, wherein the first stopping mechanism includes a latch which is rotatably attached to the first support mechanism.

10. The steering assist system of claim 1, wherein the caster cap is configured to prevent rotational movement of the at least one of the plurality of wheels in a first rotational direction and allow rotational movement of the at least one of the plurality of wheels in a second rotational direction.

11. The steering assist system of claim 1, wherein the first support mechanism includes a frame element and a frame cover, the frame element configured to be attached to a chassis of the cart.

12. A steering assist system for a cart having a plurality of wheels, the steering assist system comprising:
   an activation mechanism;
   an actuation mechanism;
   a stopping mechanism;
   a frame element having a frame cover, wherein the actuation mechanism includes a rotating lever arm configured to move within an arcuate protrusion of the frame cover; and
   wherein the activation mechanism is configured to automatically activate the actuation mechanism to move the stopping mechanism from a first position to a second position, thereby preventing rotation of at least one of the plurality of wheels.

13. The steering assist system of claim 12, including a linkage mechanism comprising:
   a rod;
   a drive pin;
   a first retaining washing and a second retaining washer;
   a first spring and a second spring; and
   wherein the first retaining washer is configured to hold the first spring captive on a first side of the drive pin, and the second retaining washer is configured to hold the second spring captive on a second side of the drive pin.

14. The steering assist system of cairn 13, wherein the linkage mechanism is connected between the actuation mechanism and the stopping mechanism.

15. The steering assist system of claim 12, including an engagement mechanism having a nautilus-shell shaped cross section, the engagement mechanism configured to contact the stopping mechanism to prevent rotation of the at least one of the plurality of wheels.

16. A cart comprising:
   a computer mounted below a horizontal work surface;
   a display screen mounted above the horizontal work surface;
   a control panel coupled to the horizontal work surface;
   at least one moveable handle;
   at least one stationary handle;
   a chassis supported on a pair of front caster wheels and a pair of rear caster wheels; and
   a steering assist system, wherein the steering assist system includes:
      an activation mechanism,
      an actuation mechanism,
      a stopping mechanism, and
      wherein the activation mechanism is configured to automatically activate the actuation mechanism to move the stopping mechanism from a first position to a second position, thereby preventing rotation of at least one of the rear caster wheels.

17. The steering assist system of claim 16, wherein when the stopping mechanism is in the second position, the at least one of the rear caster wheels is configured to abut the stopping mechanism and remain in a substantially straight orientation with respect to a forward facing direction of the cart.

* * * * *

UNITED STATES PATENT AND TRADEMARK OFFICE
CERTIFICATE OF CORRECTION

PATENT NO.         : 9,623,886 B2
APPLICATION NO.    : 15/048425
DATED              : April 18, 2017
INVENTOR(S)        : Tim Barden et al.

Page 1 of 1

It is certified that error appears in the above-identified patent and that said Letters Patent is hereby corrected as shown below:

In the Claims

Claim 14, Column 20, Line 5, "cairn 13" should read --claim 13--.

Signed and Sealed this
First Day of January, 2019

Andrei Iancu
*Director of the United States Patent and Trademark Office*